United States Patent [19]
Heller et al.

[11] Patent Number: 4,688,582
[45] Date of Patent: Aug. 25, 1987

[54] PORTABLE HAND-HELD TYMPANOMETER

[75] Inventors: James W. Heller, Camillus; Andrew J. Kugler, Syracuse; Andrew Longacre, Jr., Skaneateles; Daniel L. Williams, Liverpool, all of N.Y.

[73] Assignee: Welch Allyn, Inc., Skaneateles Falls, N.Y.

[21] Appl. No.: 836,723

[22] Filed: Mar. 6, 1986

[51] Int. Cl.$^4$ ............................................. A61B 15/00
[52] U.S. Cl. ..................................... 128/746; 73/585
[58] Field of Search ....................... 128/9, 746; 73/585

[56] References Cited

U.S. PATENT DOCUMENTS

| | | | |
|---|---|---|---|
| 3,588,358 | 6/1971 | Rudmose | 128/746 |
| 3,757,769 | 9/1973 | Arguimbau et al. | 128/746 |
| 3,882,848 | 5/1975 | Klar et al. | 128/746 |
| 4,002,161 | 1/1977 | Klar et al. | 128/746 |
| 4,009,707 | 3/1977 | Ward | 128/746 |
| 4,053,951 | 10/1977 | Hudspeth et al. | 128/671 |
| 4,057,051 | 11/1977 | Kerouac | 128/746 |
| 4,122,841 | 10/1978 | Rock et al. | 128/746 |
| 4,237,905 | 12/1980 | Keller et al. | 128/746 |
| 4,429,702 | 2/1984 | von Recklinghausen | 128/746 |
| 4,567,881 | 2/1986 | Heller | 128/746 |
| 4,602,642 | 7/1986 | O'Hara et al. | 128/736 |

Primary Examiner—Kyle L. Howell
Assistant Examiner—Randy Citrin
Attorney, Agent, or Firm—Bruns and Wall

[57] ABSTRACT

A portable, hand-held tympanometer that has the capability of performing the tympanometry and of displaying and storing the test results all within the hand-held instrument. A separate unit that is not in any way attached to the tympanometer during the testing is provided to print the test results and to recharge the tympanometer battery. The tympanometer has a body portion and a head portion to which a speculum is attached, the speculum being adapted to engage the canal of the ear being examined in sealed relation thereto. A speaker in the speculum transmits acoustic signals into the ear canal and a microphone in the speculum receives the signals that are reflected back through the canal by the tympanic membrane. A pressure transducer is located in the head portion of the tympanometer, and a miniature pump located in the body portion operates to introduce a range of pressures into the ear canal while the acoustic signals are being transmitted and received. The tympanometer also includes a liquid crystal display in the head portion which indicates the admittance of the tympanic membrane as determined by the speaker and microphone.

33 Claims, 10 Drawing Figures

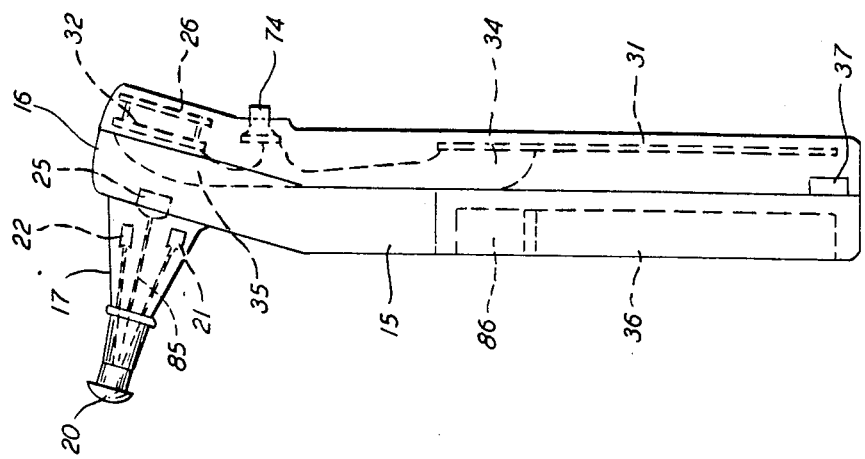
FIG. 3
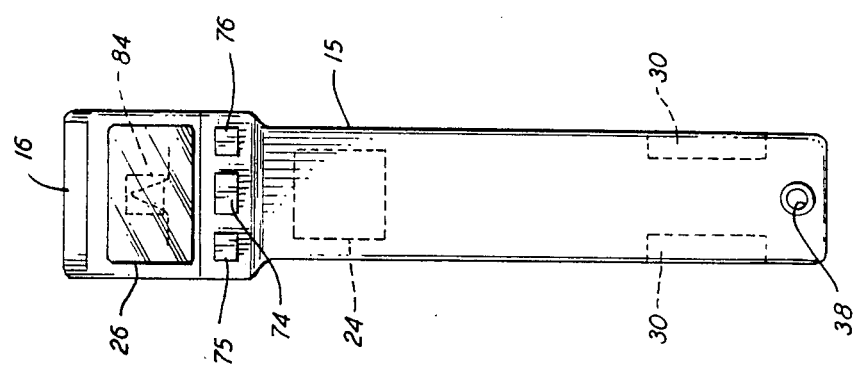
FIG. 2
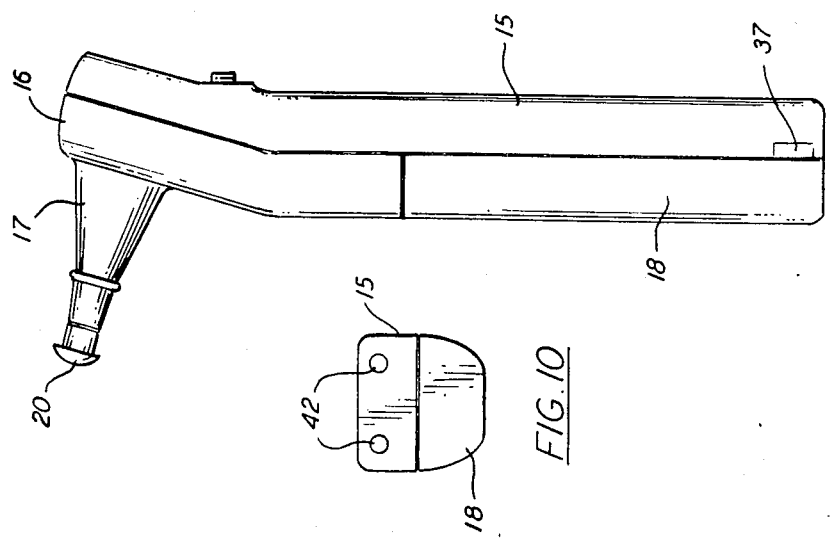
FIG. 1
FIG. 10

PORTABLE HAND-HELD TYMPANOMETER

BACKGROUND OF THE INVENTION

This invention relates generally to medical diagnostic instruments, and has particular reference to a novel portable, hand-held tympanometer and a coacting printer/charger unit.

Tympanometers are instruments that are used to measure the acoustic admittance (or "absorption") of the tympanic membrane and middle ear system over a range of pressures. Tympanometers have been commercially available since around 1958 and most of the prior art devices employ a test probe that is inserted into the patient's ear canal, the probe being maintained in position by a headset or manually by the physician or clinician administering the test.

To the best of the applicant's knowledge, in all of the tympanometers that have been developed heretofore, the ear test probe is connected by a cable to a larger, table mounted unit provided with means for displaying the test results. Some of the table mounted units also include means for recording the test results, as for example, on a chart.

A limitation on the use of the prior art tympanometers results from the fact that the ear test probe must be physically connected to the table mounted unit to produce a display of the test results and/or to have a printout of same. This means that the testing must take place in the room where the table mounted unit is located because the latter is not readily portable. Because of this, the prior art devices cannot be used by a physician in the course of making his hospital rounds, nor can they be conveniently used in certain other instances.

SUMMARY OF THE INVENTION

The present invention provides a portable, hand-held tympanometer that has the capability of performing the tympanometry and of displaying and storing the test results all within the hand-held instrument. The instrument thus has advantages over prior art devices in that it offers equivalent functions at a lower manufacturing cost, and because it is easily portable it permits greater versatility in use. A separate unit that is not in any way attached to the tympanometer during the testing is provided to print the test results and to recharge the tympanometer battery as necessary.

The tympanometer of the invention has a body portion and a head portion to which a speculum is attached, the speculum being adapted to engage the canal of the ear being examined in sealed relation thereto. A speaker in the speculum transmits acoustic signals into the ear canal and a microphone in the speculum receives the signals that are reflected back through the canal by the tympanic membrane. A pressure transducer is located in the head portion of the tympanometer, and a miniature pump located in the body portion operates to introduce a range of pressures into the ear canal while the acoustic signals are being transmitted and received.

The tympanometer also includes a liquid crystal display in the head portion which indicates the acoustic admittance of the tympanic membrane as determined by the signal from the microphone. Circuit means in the body portion permit the displayed information to be stored, and other circuit means process the signals from the transducers and control the pump and the display.

The separate printer/charger unit includes a well that is adapted to receive the body portion of the tympanometer to permit data transmission and recharging. This unit has a thermal print head with paper feed, and is also provided with an ear simulator and check window which coact to determine whether or not the tympanometer is operating properly, all of which will be described in more detail hereinafter.

BRIEF DESCRIPTION OF THE DRAWINGS

FIG. 1 is a side elevation of a tympanometer embodying the present invention;

FIG. 2 is a rear elevation of the instrument of FIG. 1;

FIG. 3 is a diagrammatic cutaway view of the instrument, corresponding to FIG. 1, showing the approximate location of various of the internal components;

FIG. 10 is a bottom plan view of the tympanometer of FIG. 1.

DESCRIPTION OF THE PREFERRED EMBODIMENT

Figure 4:
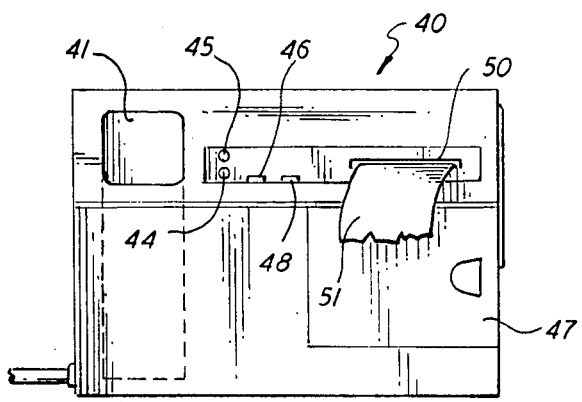
FIG. 4 is a front elevation, on a reduced scale, of the printer/charger unit.

Referring now to the drawings, and with particular reference to FIGS. 1-3, the tympanometer disclosed herein is essentially comprised of an elongated body or handle portion 15 and a head portion 16, the latter having an outwardly projecting speculum, 17 connected thereto as shown. The handle is hollow and includes a removable cover 18 that permits access to the interior of the handle. The distal end of the speculum 17 is adapted to enter the canal of the ear being examined and is provided with a removable, elastomeric tip 20 that makes a pneumatic seal between the tympanometer and ear canal. The tips 20 are available in several different sizes and after use can be quickly disconnected from the speculum and replaced with a new, clean tip.

The function of the tympanometer is to measure the admittance of the tympanic membrane and middle ear system over a range of pressures. To this end, a pair of transducers in the form of a speaker 21 and microphone 22 are mounted in the speculum 17 as indicated in FIG. 3. The speaker transmits acoustic signals of uniform frequency into the ear canal and the microphone 22 receives the signals that are reflected back through the canal by the tympanic membrane at the inner end of the canal.

Figure 6:
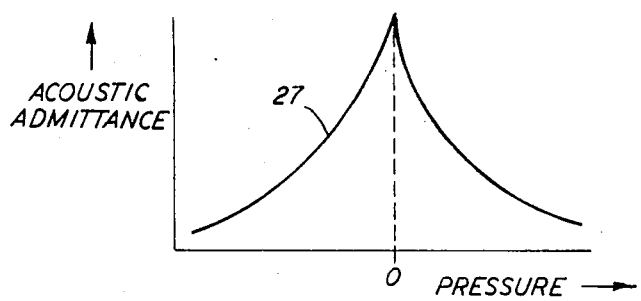
FIG. 6 is a plot or graph illustrating the compliance of a normal ear.

While the speaker 21 and microphone 22 are sending and receiving the acoustic signals, the pressure in the ear is being varied over a predetermined range of pressures by a miniature pump 24 in the body portion 15 of the tympanometer as indicated in FIG. 2, the pump pressures being measured by a pressure transducer 25, FIG. 3. The admittance of the tympanic membrane, as determined by the transducers, is displayed by a liquid crystal display (LCD) as shown at 26 in FIGS. 2 and 3 and this information is also stored in the tympanometer as will be described hereinafter. In this manner, results may be reviewed prior to printout thereby minimizing waste of time and paper on unsatisfactory test results. A normal ear shows markedly increased admittance around atmospheric pressure as is also shown by the plot 27 of FIG. 6.

The body portion 15 of the tympanometer includes two air cavities, indicated diagrammatically at 30 in FIG. 2, that provide ballast volume to limit the pressure that can be generated by the pump 24. The circuitry for the tympanometer is contained on circuit boards, the main circuit board and the LCD circuit board being shown at 31 and 32, respectively, in FIG. 3. The circuit boards are connected to each other and to the pump and transducers by printed flexible circuitry indicated at 34 and 35 in FIG. 3. The electrical power for the instrument is provided by a rechargeable nickel-cadmium battery 36, FIGS. 3 and 8, and external charging contacts are located at the lower end of the body portion 15, one of which is shown at 37 in FIG. 1. The tympanometer is also provided with a charging socket 38, FIG. 2, for receiving a jack connected to a conventional direct lug-in transformer (not shown).

Figure 5:
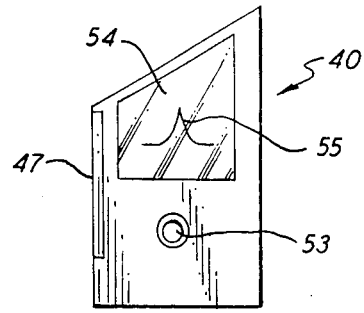
FIG. 5 is a right side elevation of the unit of FIG. 4.

The tympanometer is adapted to coact with a printer/charger unit generally indicated at 40 in FIGS. 4 and 5. This unit functions as a battery recharger and also as the means to provide a printout of the information displayed by the LCD 26. The unit 40 has a well 41 for receiving the body or handle portion 15 of the tympanometer and when the latter is positioned in the well the charging contacts 37 will engage mating contacts (not shown) in the well. The well contacts are in circuit with conventional recharging circuitry (not shown) in the unit 40. At the bottom of the tympanometer there are a pair of printer contacts 42, FIG. 10, which engage mating printer contacts (not shown) at the bottom of the well when the tympanometer is positioned therein.

The printer/charger unit 40 has a power-on indicator light 44, FIG. 4, and charge indicator light 45. When it is desired to obtain a printout of the test information stored in the tympanometer, the handle portion is inserted into the well and a print button 46 is depressed and the stored information is instantly transmitted to circuitry (not shown) in the unit 40 and at the same time the print mechanism is actuated to provide the printout. The operator, therefore, has the ability to review results on the display or start another test while the printout is being made. The print mechanism comprises a commercially available thermal print head which coacts with a conventional paper feed, neither of which is shown.

Paper is loaded into the printer/charger unit through an access door 47 and by depressing a paper feed button 48 the paper is automatically fed through a guide mechanism to the thermal print head. Thereafter, the paper feed occurs automatically whenever the print button 46 is depressed. The printout that is produced leaves the unit through a slot 50 and is as shown at 51 in FIG. 7. These printouts are to be described in more detail hereinafter.

In addition to its printing and recharging functions, the unit 40 provides an ear simulator device and a check window which are used to determine whether or not a particular tympanometer is working properly. The ear simulator is a small air cavity (not shown) in the unit that has an entrance port 53, FIG. 5, which is engaged by the speculum tip 20 in the same fashion that the latter engages the human ear canal. The cavity has a flexible membrane termination, and the properties of the cavity and membrane are such that they accoustically simulate a normal human ear, and can be reliably adjusted for peak admittance and remain stable over a long period of time. In use, the speculum tip is inserted into the port 53 and a compliance test is conducted just as though it were a test on a human ear.

A printout is obtained from the ear simulator test and this printout is inserted into a pocket behind the check window 54, FIG. 5, which is a piece of transparent material such as glass or clear plastic. The check window itself has a normal compliance plot 55 printed or etched thereon and by comparing this with the plot derived from the ear simulator test it can be determined whether or not the instrument is working properly. While the above-described instrument check can be carried out in a matter of minutes, it need not be done prior to every human ear test. For example, if the tympanometer has been positioned in the printer/charger unit well 41 for a time and is to be used to test a group of school children, it probably will be checked before testing the group but not between each individual test.

Figure 9:
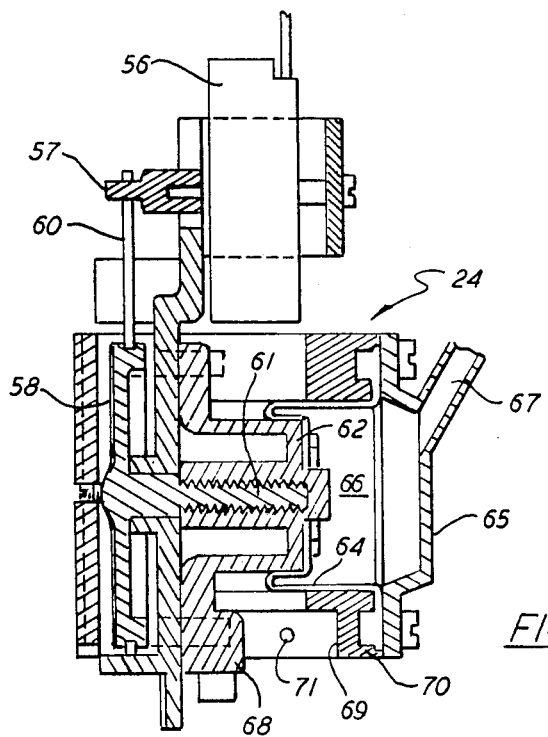
FIG. 9 is an enlarged, vertical sectional view through the miniature pump.

Reference is now made to FIG. 9 which shows the miniature pump 24 and its motor 56 in section. The pump is a diaphragm type that provides both positive and negative pressure to the ear. The pump motor is reversible and drives a motor pulley 57 which in turn drives a pump pulley 58 through a drive belt 60. The pump pulley has a central worm portion 61 that extends into the interior of the pump where it threadedly engages a piston 62. The piston 62 is connected to a rolling diaphragm 64 that together with a cover plate 65 defines a sealed pressure chamber 66.

The chamber 66 has an outlet 67 that is connected by an outlet tube (not shown) to the pressure tube 85 located in speculum 17. With this arrangement, it will be apparent that the pump motor 56 can be driven in one direction to increase the pressure in the chamber 66 and in the opposite direction to decrease the pressure, thereby providing both positive and negative pressure to the ear.

As will be described in more detail hereinafter, the pump 24 must be in its center or atmospheric pressure position at the start of a test. To this end, the pump piston 62, FIG. 9, has a projection or "flag" 68 that rides back and forth in a slot 69 in the pump housing 70 as the pump is operating. The flag is constructed so that the optical beam is interrupted when the piston is above center position and uninterrupted when it is below center position. The position of the flag is sensed by an optical interrupter that is shown diagrammatically at 71 and this enables the circuitry in the tympanometer to move the pump piston to center position as required because of limited pump stroke.

Figure 8:
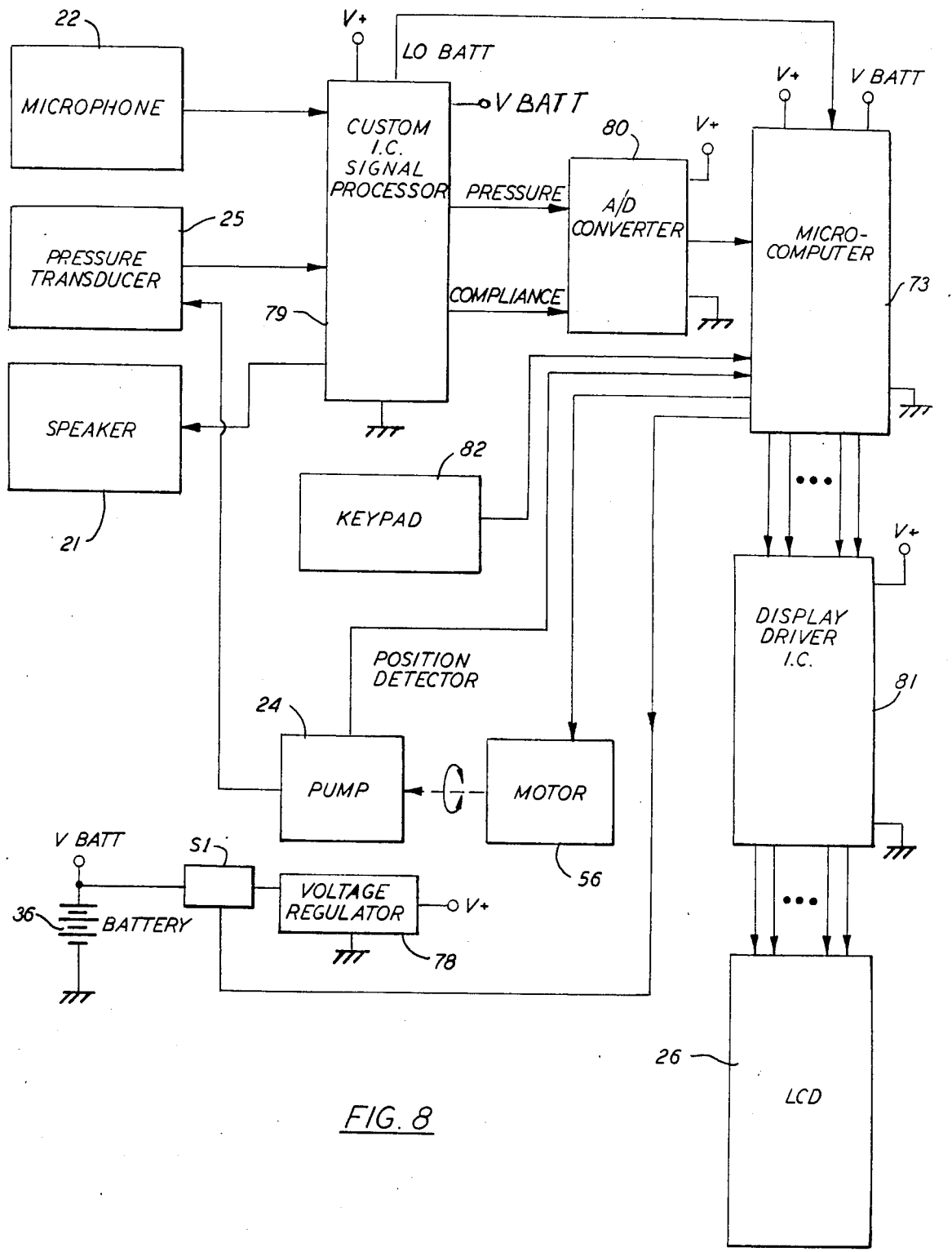
FIG. 8 is a block diagram of the electronic circuitry of the tympanometer.

The sequence of operation of the tympanometer is controlled by a micro-computer 73, FIG. 8, having the control information contained in its stored program. Operation is initiated by depressing a START/RUN button 74, FIGS. 2 and 3 on the back or physician's side of the tympanometer, the button being part of the keypad 82 in FIG. 8. The pressure system is vented to atmospheric pressure by a valve 86 at the end of each test or attempted test and the pump is returned to its center position. After an aborted test, the valve is reclosed and another test is automatically started. The automatic re-start is faster, requires less ballast and a shorter pump stroke than continuous pumping methods thereby enabling the instrument to be a portable, hand-held size. If, for some reason, the instrument is not properly vented and remains pressurized, a pressure range error symbol will be displayed by the LCD 26.

Depressing the START/RUN button 74 to initiate a test also causes the admittance signal to be checked. Thus, admittance values below a predetermined limit cause a BLOCK error symbol to be displayed while values over a second limit cause an OVER error symbol to be displayed. If the compliance is between these two limits, the pump 24 is started by the micro-computer 73 in the pressurization direction and the pressure signal is monitored. If the pressure does not reach a predetermined value by prescribed time limits, a LEAK error symbol will be displayed by the LCD and the pump piston will be returned to center position. The LEAK error symbol normally would appear because a good seal has not been achieved between the speculum tip 20 and the ear canal.

If the pressure reaches 200 daPa within the prescribed time limit, the pump motor is turned off by the micro-computer and there is a pause to allow the system to settle. This is done so that no interference is introduced by the pump during determination of ear canal volume and is important because an error in the ear canal volume will shift the entire tympanometric curve. Thereafter, successive admittance readings are made and averaged, and the average value is used as the ear canal volume or equivalent volume at +200 daPa. This averaging reduces error due to patient movement, extraneous noise and so forth. This ear canal volume is subtracted by the micro-computer from each actual reading during the test sweep because what is wanted is a plot or tympanic membrane admittance rather than a plot that includes the entire air volume in the ear canal.

Figure 7:
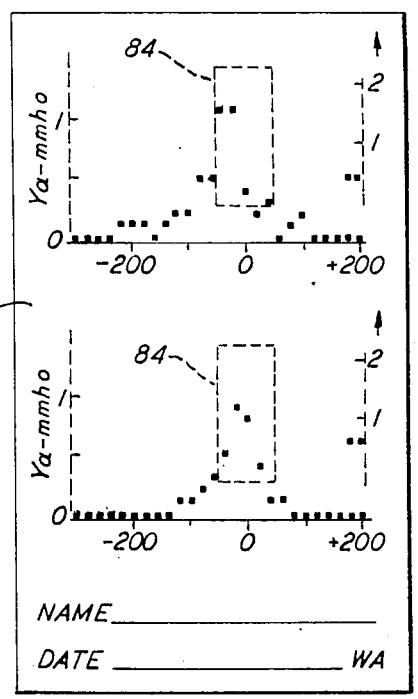
FIG. 7 illustrates a printer/charger unit printout indicating the compliance of the patient's left and right ears.

After the ear canal volume has been determined, the pump 24 is driven in the vacuum direction by the micro-computer and pressure is monitored. Admittance readings are taken at 20 daPa intervals and displayed by the LCD until −300 daPa has been reached. This results in a total of 26 readings resulting in a plot as shown in FIGS. 2 and 7. Upon reaching −300 daPa, the pump piston is returned by the micro-processor to center position. If, however, any of the 26 readings have not been taken within a prescribed time, a LEAK error symbol is displayed After the test has been completed and a plot is displayed. by the LCD as shown in FIG. 2, either the left STORE/RECALL button 75 (when the left ear has been tested) or the right STORE/RECALL button 76 (for the right ear) is depressed which causes the displayed information to be stored in the micro-computer 73. After both ears have been tested, the normal procedure is to place the tympanometer in the well 41 of the printer/charger unit 40, FIGS. 4 and 5, described above. Thereafter, the print button 46 is depressed which results in a printout 51 as shown in FIG. 7, the printout having indicia (not shown) to show which plot is for which ear. It should be noted in this connection that as soon as the print button is depressed the tympanometer can be removed from the printer/charger unit and used for another test, without waiting for the printout 51 to be completed.

After a test has been completed and the results stored in the tympanometer, depressing either the left or right button 75 or 76 will cause its display to re-appear on the LCD 26. If, on the other hand, either button is depressed for more than 3 seconds, the stored information will be erased altogether. Each button 75 and 76 thus has the capability of instituting three different functions, i.e., store, recall and erase.

Reference is now made to FIG. 8 which illustrates the electronic circuitry that controls the operation, processes the signals and displays information for the tympanometer. The circuitry is powered by a battery 36, FIGS. 3 and 8. The micro-computer 73 is connected directly to the battery and is always "ON" in a standby mode. When the START/RUN button 74 is depressed, it provides an input to the micro-computer which causes the latter to change to a "RUN" mode and switches battery power to a voltage regulator 78 through switch S1. The circuitry other than the micro-computer is powered by the voltage regulator and is therefore turned on when the START/RUN button is actuated.

The signals that are transmitted and received by the speaker 21 and microphone 22, FIGS. 3 and 8, in the speculum 17 are generated and processed by a custom integrated circuit 79, FIG. 8. A 226 Hz sine-wave is digitally synthesized to drive the speaker. The speaker drive is amplitude modulated by an operational transconductance amplifier (OTA) having gain controlled by an automatic gain control (AGC) output.

The microphone output first passes through a pre-amplifier and then 226 Hz band-pass filter to reduce extraneous noises. The signal is then full-wave rectified by a precision operational amplifier rectifier. Finally, the signal is low-pass filtered to produce a D.C. signal proportional to admittance. This signal is also used to control the OTA gain, thereby forming an AGC loop.

The output of the pressure transducer 25, is also amplified and low-pass filtered by the custom integrated circuit 79. The analog pressure and admittance signals from the circuit 79 are fed into an analog to digital (A/D) converter 80. The A/D digital output is fed to the micro-computer 73. The program within the micro-computer read-only-memory (ROM) controls the operation of the instrument. A random-access-memory (RAM) in the micro-computer is utilized to store the results of tests.

The micro-computer 73 controls the LCD 26, FIGS. 2 and 8, by means of a display driver integrated circuit 81. This circuit minimizes the number of electrical connections between the display area and the micro-computer. The LCD consists of 16 rows, 26 columns and special symbols. This produces a display that displays tympanometric test results with a minimum number of display elements, the display being made up of a series of unconnected dots as indicated in FIGS. 2 and 7.

The miniature pump 24 has a two-way communication with the micro-computer 73 which can drive the pump motor 56 in either direction and at variable speeds by means of a dual, power operational amplifier circuit. As noted above, the position of the pump piston 62, FIG. 9, is sensed by an optical interrupter 71 and transmitted to the micro-computer. The pump can therefore be returned to center position by driving the motor in the appropriate direction until a change in the status of the optical interrupter output is detected.

The condition of the battery 36 is monitored continuously and a low indication causes testing to be disabled and an error symbol displayed on the LCD. The monitoring is carried out by the custom integrated circuit 79 which, by means of a comparator circuit and an internal reference voltage, provides an output to the micro-computer 73 indicating whether the battery is above or below the required level.

In FIG. 8, the keypad 82 contains the START/RUN and STORE/RECALL/ERASE switches which all input to the micro-computer.

Referring once again to the LCD 26 in FIG. 2 and the printout 51 of FIG. 7, it can be seen that there is an outline 84 that contains within its borders a "target" area. This area is important because the apex or peak of the admittance plot for a normal ear should appear inside the target area. The relationship of the peak to the target area is diagnostically significant. Different target areas may be provided for different patient populations and/or operating parameters.

The tympanometer disclosed herein is provided with suitable means (not shown) for isolating pump noise from the three transducers in the speculum, such being necessary for proper performance of the instrument, including acoustic reasonators coacting with the ballast volume and acoustic attenuators and vibration absorbing material. While the typmanometer has been described as being used in conjunction with the printer/charger unit 40 shown in FIGS. 4 and 5, the tympanometric results can, if necessary, be tele-communicated by known technology to a remote location.

From the foregoing description it will be apparent that the invention provides a novel tympanometer having substantial advantages over the prior art. As will be understood by those familiar with the art, the invention may be embodied in other specific forms without departing from the spirit or essential characteristics thereof.

We claim:

1. A portable hand-held auditory instrument comprising a casing, a speculum on said casing and including means to sealably engage the canal of an ear being examined, means in the speculum for emitting signals into the ear canal, means in the speculum to receive the signals reflected back through the canal by a tympanic membrane, a pressure transducer in the speculum; and means in the casing for introducing variable positive and negative pressures into the canal while said signals are being transmitted and received, wherein the last-mentioned means includes a rolling diaphragm pump of the type having a moving piston and a flexible rolling diaphragm connected to said piston and to a cover plate to define a pressure chamber.

2. The auditory instrument of claim 1 in which said pump further includes a reversible electric motor, a screw worm that extends into the piston to drive the same, and means rotationally coupling the motor and the screw worm.

3. The auditory instrument of claim 1 further comprising means for sensing the position of said piston.

4. The auditory instrument of claim 3 further including a pressure relief valve for automatically relieving pressure between said pump and said ear canal and closing when said position sensing means senses that said piston has returned to a center position.

5. The auditory instrument of claim 4 further comprising means for automatically restarting said pump after said valve has closed and said piston has returned to its center position.

6. A portable hand-held tympanometer comprising a unitary casing which consists of a head-and-handle portion and a speculum integral with the casing head-and-handle portion; the speculum including means to engage in sealed relation the canal of an ear being examined; means in the speculum for transmitting acoustic signals into the ear canal; means in the speculum for receiving acoustic signals reflected back through the canal by the tympanic membrane at the inner end of the canal; a pressure transducer in the speculum; pump means in the casing head-and-handle portion for introducing variable pressures into the ear canal while said auditory signals are being transmitted and received; and information display means situated on the casing head-and-handle portion for indicating the admittance of the tympanic membrane as determined by the signal transmitting and receiving means and the pressure transducer.

7. A tympanometer as defined in claim 6 wherein the casing has a body portion and a head portion connected to the body portion.

8. A tympanometer as defined in claim 6 wherein the signal transmitting means is a speaker.

9. A tympanometer as defined in claim 6 wherein the signal receiving means is a microphone.

10. A tympanometer as defined in claim 6 wherein said pump means includes a single pump having an outlet capable of selectively delivering both positive and negative pressure to the ear canal.

11. A tympanometer as defined in claim 10 in which said pump means further includes at least one air ballast means in said head-and-handle portion for acoustically isolating the receiving means from the pump.

12. A tympanometer as defined in claim 6 wherein the display means is a liquid crystal display.

13. A tympanometer as defined in claim 6 together with means in the casing for storing the information displayed by the information display means.

14. A tympanometer as defined in claim 6 together with a printer unit means that coact with the tympanometer and includes means for producing a printout of the information displayed by the display means.

15. A tympanometer as defined in claim 6 wherein said pump means include a relief valve for relieving pressure being introduced into said canal, and further comprising control means for automatically opening said valve if the measured admittance of the ear indicates that said engaging means has not achieved a good seal, and then closing said valve and restarting said pump to reattempt a measurement of admittance.

16. A tympanometer as defined in claim 6 further comprising means for detecting a leak in the sealing relationship of said speculum and said canal, and automatically effecting a neutral pressure in said canal and restarting said pump to reattempt a measurement of admittance.

17. A self-contained, portable, hand-held tympanometer comprising a casing that includes a combined handle-and-head portion and a speculum integral with the casing handle-and-head portion, the speculum including means to enter the canal of an ear being examined; a pliable removable tip at a distal end of the speculum for effecting sealing engagment between the speculum and the ear canal; means in the speculum for transmitting acoustic signals into the ear canal; means in the speculum for receiving acoustic signals reflected back through the canal by the tympanic membrane at the inner end of the canal; a pressure transducer in the speculum; pump means in the casing head-and-handle portion for introducing variable pressures into the ear canal while said acoustic signals are being transmitted and received; and information display means situated on the casing head-and-handle portion for indicating the admittance of the tympanic membrane as determined by the signal transmitting and receiving means and the pressure transducer.

18. A tympanometer as defined in claim 17 wherein the signal transmitting and signal receiving means are a speaker and a microphone, respectively.

19. A tympanometer as defined in claim 17 wherein the pump means includes a single pump situated in the head-and-handle portion of the casing and having an outlet selectively delivering both positive and negative pressure to the ear canal.

20. A tympanometer as defined in claim 17 wherein the display means is a liquid crystal display.

21. A tympanometer as defined in claim 17 together with means in the casing for storing the information displayed by the information display means.

22. A tympanometer as defined in claim 17 together with a printer unit means that coact with the tympanometer and includes means for producing a printout of the information displayed by the display means.

23. A tympanometer as defined in claim 22 wherein the printer unit has a well for receiving the head-and-handle portion of said tympanometer casing and electrical contact means in said well for contacting mating contact means on said tympanometer only when the latter is disposed in said well.

24. A tympanometer as defined in claim 17 together with a rechargeable battery in the casing for providing electrical power for the tympanometer.

25. A tympanometer as defined in claim 24 together with a printer/charger unit that coacts with the tympanometer and includes means for recharging the battery and means for producing a printout of the information displayed by the display means.

26. A portable, hand-held tympanometer comprising a hand-holdable casing; a speculum integral with said casing and including means for entering the canal of an ear being examined; a pliable tip at a distal end of the speculum for effecting sealing engagement between the speculum and the ear canal; means in the speculum for transmitting signals into the ear canal; means in the speculum for receiving signals reflected back through the canal by the tympanic membrane at the inner end of the canal; a pressure transducer in the speculum; pump means in the casing for introducing variable pressures into the ear canal while said signals are being transmitted and received; wherein the pump means include a piston and means for sensing the position of the piston; and information display means on said casing for indicating the admittance of the tympanic membrane as determined by the signal transmitting and receiving means and the pressure transducer.

27. A tympanometer as defined in claim 26 wherein the position sensing means includes a "flag" on the pump piston and optical interrupter that coacts with the "flag."

28. A portable, hand-held tympanometer comprising a body portion and a head portion connected to the body portion; a speculum connected to the head portion, the speculum being adapted to enter the canal of the ear being examined; a pliable, removable tip at a distal end of the speculum for effecting sealing engagement between the speculum and the ear canal; a first transducer means in the speculum for transmitting acoustic signals into the ear canal; a second transducer means in the speculum for receiving the acoustic signals that are reflected back through the canal by the tympanic membrane at the inner end of the canal; a pressure transducer in the speculum; a pump in the body portion for introducing a range of pressures into the ear canal through the pressure transducer while said acoustic signals are being transmitted and received; information display means in the head portion for indicating the admittance of the tympanic membrane as determined by the signal transmitting and receiving means and the pressure transducer; means in the body portion for storing the information displayed by the information display means; and circuit means in the tympanometer body portion and head portion for processing signals from the transducers and controlling the pump and display means.

29. A tympanometer as defined in claim 28 wherein the pump is a rolling diaphragm-type pump having a moving piston whereby the pump can provide both positive and negative pressures to the ear canal.

30. A tympanometer as defined in claim 29 including means for sensing the position of the pump piston.

31. A tympanometer as defined in claim 30 wherein the position sensing means includes a "flag" on the pump piston and an optical interrupter that coacts with the "flag".

32. A tympanometer as defined in claim 28 further including manually actuable switch means actuable to store, recall, or erase the displayed information.

33. A tympanometer as defined in claim 28 including means for turning off the pump after it has produced a predetermined pressure within a prescribed time limit, means for delaying further pump action for a prescribed time interval, means for making and averaging a predetermined number of admittance readings, and means for thereafter reactivating the pump.

* * * * *